(12) United States Patent
Zamborini et al.

(10) Patent No.: US 8,153,439 B2
(45) Date of Patent: Apr. 10, 2012

(54) CHEMICAL SENSORS FOR DETECTING VOLATILE ORGANIC COMPOUNDS AND METHODS OF USE

(75) Inventors: Francis P. Zamborini, Louisville, KY (US); Francisco J. Ibanez, Louisville, KY (US)

(73) Assignee: University of Lousiville Research Foundation, Inc., Louisville, KY (US)

( * ) Notice: Subject to any disclaimer, the term of this patent is extended or adjusted under 35 U.S.C. 154(b) by 0 days.

(21) Appl. No.: 12/279,950

(22) PCT Filed: Jul. 26, 2008

(86) PCT No.: PCT/US2008/071275
§ 371 (c)(1),
(2), (4) Date: Aug. 19, 2008

(87) PCT Pub. No.: WO2009/015378
PCT Pub. Date: Jan. 29, 2009

(65) Prior Publication Data
US 2010/0225337 A1    Sep. 9, 2010

Related U.S. Application Data

(60) Provisional application No. 60/952,125, filed on Jul. 26, 2007.

(51) Int. Cl.
*G01N 33/00*    (2006.01)
(52) U.S. Cl. ....... 436/127; 422/98; 422/68.1; 422/82.01
(58) Field of Classification Search .................. 436/127; 422/98, 68.1, 82.01
See application file for complete search history.

(56) References Cited

U.S. PATENT DOCUMENTS

| | | | |
|---|---|---|---|
| 5,186,860 A | 2/1993 | Joyce, Jr. et al. | |
| 5,879,631 A | 3/1999 | Wewers et al. | |
| 6,134,946 A * | 10/2000 | Liu et al. | 73/31.06 |
| 6,537,498 B1 | 3/2003 | Lewis et al. | |
| 2005/0079551 A1 | 4/2005 | Mizuno et al. | |
| 2005/0245753 A1 | 11/2005 | Cruse et al. | |
| 2006/0014005 A1* | 1/2006 | Basco et al. | 428/209 |
| 2007/0240491 A1 | 10/2007 | Pavlovsky et al. | |

OTHER PUBLICATIONS

Ahn et al., "Easy Synthesis and Magnetic Properties of Iron Oxide Nanoparticles," Chem. Mater., 16, 2004, pp. 3274-3278.
Albert et al., "Cross-Reactive Chemical Sensor Arrays," Chem. Rev., 100, 2000, pp. 2595-2626.
Ananikov et al., "New Approach for Size-and Shape-Controlled Preparation of Pd Nanoparticles with Organic Ligands, Synthesis and Application in Catalysis," J. Am. Chem. Soc., 129, 2007, pp. 7252-7253.
Bevenot et al., "Hydrogen leak detection using an optical fibre sensor for aerospace applications," Sens. Actuators B, 67, 2000, 57-67.

(Continued)

*Primary Examiner* — Jill Warden
*Assistant Examiner* — Monique Cole
(74) *Attorney, Agent, or Firm* — Stites & Harbison PLLC; Terry L. Wright (57) ABSTRACT

The presently-disclosed subject matter provides sensors and methods for detecting volatile organic compounds (VOCs) by determining the conductivity of a chemiresistant film upon exposure to VOCs, including for example chemiresistant films comprised of surfactant-coated metal alloy nanoparticles.

18 Claims, 6 Drawing Sheets

OTHER PUBLICATIONS

Bohne et al., "N-Acylureido Functionality as Acceptor Substituent in Solvatochromic Fluorescence Probes: Detection of Carboxylic Acids, Alcohols, and Fluoride ions," J. A. Chem. Soc. 127, 2005, pp. 17158-17159.

Briglin et al., "Detection of Organic Mercaptan Vapors Using Thin Films of Alkylamine-Passivated Gold Nanocrystals," Langmuir., 20, 2004, pp. 299-305.

Brust et al., Self-Assembled Gold Nanoparticle Thin Films with Nonmetallic Optical and Electronic Properties, Langmuir., 14, 1998, pp. 5425-5429.

Brust et al., "Synthesis of Thiol-derivatised Gold Nanoparticles in a Two-phase Liquid-Liquid System," Chem. Comm., 7, 1994, pp. 801-802.

Cai et al., "Dual-Chemiresistor GC Detector Employing Monolayer-Protected Metal Nanocluster Interfaces," Anal. Chem., 74, 2002, pp. 3533-3539.

Cao et al., "Breath Analysis: Potential for Clinical Diagnosis and Exposure Assessment," Clin. Chem., 52, 2006, pp. 800-811.

Che et al., "Carbon nanotubule membranes for electrochemical energy storage and production," Nature, 393, 1998, pp. 346-349.

Choi et al., "Dynamics of CO2-Plasticized Electron Transport in Au Nanoparticle Films: Opposing Effects of Tunneling Distance and Local Site Mobility," J. Phys. Chem., 111, 2007, pp. 3778-3785.

Christofides et al., "Solid-state sensors for trace hydrogen gas detection," J. Appl. Phys. 68, 1990, pp. 1-30.

Crooks et al., "New Organic Materials Suitable for Use in Chemical Sensor Arrays," Acc. Chem. Res., 31, 1998, pp. 219-227.

Dankert et al., "Hydrogen-induced percolation in discontinuous films," Appl. Phys. Lett, 81, 2002, pp. 1618-1620.

David et al., "Molecular-wire behaviour in p-phenylenevinylene oligomers," Nature, 396, 1998, pp. 60-63.

Drew et al., "An Electronic Nose Transducer Array of Vapoluminescent Platinum(II) Double Salts," J. Am. Chem. Soc., 123, 2001, pp. 8414-8415.

Dutta et al., "Tea quality prediction using a tin oxide-based electronic nose: an artificial intelligence approach," Sens. Actuators B, 94, 2003, pp. 228-237.

Dwivedi et al., "Sensing properties of palladium-gate MOS (Pd-MOS) hydrogen sensor-based on plasma grown silcone dioxide," Sens. Actuators B, 71, 2000, pp. 161-168.

Eklund et al., "Synthesis and Catalytic Properties of Soluble Platinum Nanoparticles Protected by a Thiol Monolayer," Langmuir, 20, 2004, pp. 6012-6018.

Evans et al., "Vapour sensing using hybrid organic-inorganic nanostructured materials," Mater. Chem., 10, 2000, pp. 183-188.

Favier et al., "Hydrogen Sensors and Switches from Electrodeposited Palladium Mesowire Arrays," Science, 293, 2001, pp. 2227-2231.

Finlayson-Pitts et al., "Tropospheric Air Pollution: Ozone, Airobrne Toxics, Polycyclic Aromatic Hydrocarbons, and Particles," Science, 276, 1997, p. 1045-1052.

Foos et al., "Thiol-Terminated Di-, Tri-, and Tetraethylene Oxide Functionalized Gold Nanoparticles: A Water-Soluble, Charge-Neutral Cluster," Chem. Mater., 14, 2002, pp. 2401-2408.

Ganesan et al., "Monodisperse Thioether-Stabilized Palladium Nanoparticles: Synthesis, Characterization, and Reactivity," Chem. Mater., 19(14), 2007, pp. 3464-3471.

Gopel, W, "Chemical imaging: I. Concepts and visions for electronic and bioelectronic noses," Sens. Actuators B., 52, 1998, pp. 125-142.

Grate, J.W., "Acoustic Wave Microsensor Arrays for Vapor Sensing," Chem. Rev., 100, 2000, pp. 2627-2648.

Grate et al., "Sorptive Behavior of Monolayer-Protected Gold Nanoparticle Films: Implications for Chemical Vapor Sensing," Anal. Chem., 75, 2003, pp. 1868-1879.

Han et al., "Core-Shell Nanostructured Nanoparticle Films as Chemically Sensitive Interfaces," Anal. Chem., 73, 2001, pp. 4441-4449.

Han et al., "Nanoparticle-structured sensing array materials and pattern recognition for VOC detection," Sens. Actuators B, 106, 2005, pp. 431-441.

Harnack et al., "Lithographic patterning of nanoparticle films self-assembled from organic solutions by using a water-soluble mask," Appl. Phys. Lett., 86, 2005, 034108-034108-3.

Horinouchi et al., "Hydrogen Storage Properties of Isocyanide-Stabilized Palladium Nanoparticles,". Langmuir 2006, 22, 1880-1884.

Hostetler et al., "Dynamics of Place-Exchange Reactions on Monolayer-Protected Gold Cluster Molecules," Langmuir, 15, 1999, pp. 3782-3789.

Hostetler et al., "Stable, Monolayer-Protected Metal Alloy Clusters," J. Am. Chem. Soc., 120, 1998, pp. 9396-9397.

Huang et al., "Pd-Ni thin films grown on porous Al2O3 substrates by metalorganic chemical vapor deposition for hydrogen sensing," Thin Solid Films, 345, 1999, pp. 217-221.

Hughes et al., "Thin films of Pd/Ni alloys for detection of high hydrogen concentrations," J. Appl. Phys., 71, 1992, pp. 542-544.

Hughes et al., "Thin-film palladium and silver alloys and layers for metal-insulator-semiconductor sensors," J. Appl. Phys., 62, 1987, pp. 1074-1083.

Ibanez et al., "Ozone-and Thermally Activated Films of Palladium Monolayer-Protected Clusters for Chemiresistive Hydrogen Sensing," Langmuir, 22, 2006, pp. 9789-9796.

Ibanez et al., "Chemiresistive Vapor Sensing with Microscale Films of Gold Monolayer Protected Clusters," Anal. Chem., 78, 2006, pp. 753-761.

Isaacs et al., "Synthesis of Tetraoctylammonium-Protected Gold Nanoparticles with Improved Stability," Langmuir, 21, 2005, pp. 5689-5692.

Jana et al., "Wet Chemical Synthesis of High Aspect Ratio Cylindrical Gold Nanorods," J. Phys. B., 105, 2001, pp. 4065-4067.

Joseph et al., "Self-Assembled Gold Nanoparticle/Alkanedithiol films: Preparation, Electron Microscopy, XPS-Analysis, Charge Transport, and Vapor-Sensing Properties," Phys. Chem. B, 107, 2003, pp. 7406-7413.

Joseph et al., "Chemiresistor coatings from Pt-and Au-nanoparticle/ nanoedithiol films: sensitivity to gases and solvent vapors," Sens. Actuators B, 98, 2004, pp. 188-195.

Joseph et al., "Gold-nanoparticle/organic linker films: self-assembly, electronic and structural characterisation, composition and vapour sensitivity," Faraday Discuss., 125, 2004, pp. 77-97.

Kalli et al., "Characterization of reflectivity inversion, a- and b-phase transitions and nanostructure formation in hydrogen activated thin Pd films on silicon based substrates," Appl. Phys., 91, 2002, pp. 3829-3840.

Kalli et al., "Temperature-induced reflectivity changes and activation of hydrogen sensitive optically thin palladium films on silicon oxide," Rev. Sci. Instrum., 69, 1998, pp. 3331-3338.

Kallo et al., "Conductance and Methanol Crossover Investigation of Nafion Membranes in a Vapor-Fed DMFC," J. Electrochem. Soc., 150, 2003, pp. 765-769.

Kaltenpoth et al., "Multimode Detection of Hydrogen Gas Using Palladium-Covered Silicon-Channels," Anal. Chem., 75, 2003, pp. 4756-4765.

Kang et al., "Comparison and analysis of Pd- and Pt-GaAs Schottky diodes for hydrogen detection," J. Appl. Phys., 75, 1994, pp. 8175-8181.

Kolmakov et al., "Enhanced Gas Sensing by Individual SnO Nanowires and Nanobelts Functionalized with Pd Catalyst Particles," Nano Lett, 5, 2005, pp. 667-673.

Wolfe et al., "Fabrication of palladium-based microelectronic devices by microcontact printing," Appl. Phys. Lett., 80, 2002, pp. 2222-2224.

Wuelfing et al., "Electronic Conductivity of Solid-State, Mixed-Valent, Monolayer-Protected Au Clusters," J. Am. Chem. Soc., 122(46), 2000, pp. 11465-11472.

Yang et al., "Porous shape Persistent Fluorescent Polymer Films: An Approach to TNT Sensory Materials," J. Am. Chem. Soc., 120, 1998, pp. 5321-5322.

Yang et al., "Nerve Agents Detection Using a Cu/l-Cysteine Bilayer-Coated Microcantilever," J. Am. Chem. Soc., 125, 2003, pp. 1124-1125.

Yinon, J., "Detection of Explosives by Electronic Noses: Handheld chemical-sensing systems come in several varieties and offer advantages over the traditional bomb-sniffing dog," Anal. Chem., 2003, 99A-105A.

Yu et al., "Fabrication of Palladium Nanotubes and Their Application in Hydrogen Sensing," Chem. Mater., 17, 2005, pp. 3445-3450.

Yun et al., "Electrochemically Grown Wires for Individually Addressable Sensor Arrays," Nano Lett., 4, 2004, pp. 419-422.

Zamborini et al., "Synthesis, Characterization, Reactivity, and Electrochemistry of Palladium Monolayer Protected Clusters," Langmuir, 17, 2001, pp. 481-487.

Zamborini et al., A"Electron Hopping Conductivity and Vapor Sensing Properties of Flexible Network Polymer Films of Metal Nanoparticles," Am. Chem. Soc., 124, 2002, pp. 8958-8964.

Zamborini et al., "Distance-dependent electron hopping conductivity and nanoscale lithograpy of chemically-linked gold monolayer protected cluster films," Anal. Chim. Acta, 496, 2003, pp. 3-16.

Zhang et al., "Ozonolysis Is the Primary Cause of UV Photooxidation of Alkanethiolate Monolayers at Low Irradiance," J. Am. Chem. Soc., 120, 1998, pp. 2654-2655.

Zhang et al., "Ultraviolet Photochemistry and ex Situ Ozonolysis of Alkanethiol Self-Assembled Monolayers on Gold," Chem. Mater., 11, 1999, pp. 2191-2198.

Zhao et al., "Annealing enhanced hydrogen absorption in nanocrystalline Pd/Au sensing film," J. Appl. Phys., 97, 2005, pp. 124301-124301-7.

Zhao et al., "All-Optical Hydrogen-Sensing Materials Based on Tailored Palladium Alloy thin Films," Anal. Chem., 76, 2004, pp. 6321-6326.

Zhao et al., "All-optical hydrogen sensor based on a high alloy content palladium thin film," Sens Actuators B 2006, 113, 532-538.

Ancona et al., "Scaling Properties of Gold Nanocluster Chemiresistor Sensors," IEEE Sensors Journal, 6, 2006, pp. 1403-1414.

ISA/US, International Search Report and Written Opinion for international application No. PCT/US08/71275, mailed Oct. 2, 2008.

Kong et al., "Functionalized Carbon Nanotubes for Molecular Hydrogen Sensors," Adv. Mater., 13, 2001, pp. 1384-1386.

Krasteva et al., "Self-Assembled Gold Nanoparticle/Dendrimer Composite Films for Vapor Sensing Applications," Nano Lett., 2, 2002, pp. 551-555.

Krasteva et al., "Gold nanoparticle/PPI-dendrimer based chemiresistors Vapor-sensing properties as a function of the dendrimer size," Sens. Actuators B, 92, 2003, pp. 137-143.

Krasteva et al., "Vapor Sorption in Self-Assembled Nanoparticle/Dendrimer Films Studied by Specular Neutron Reflectometry," Langmuir, 19, 2003, pp. 7754-7760.

Lavrik et al., "Cantilever transducers as a platform for chemical and biological sensors," Rev. of Sci. Inst., 75, 2004, pp. 2229-2253.

Leff et al., "Synthesis and Characterization of Hydrophobic, Organically,-Soluble Gold Nanocrystals Functionalized with Primary Amines," Langmuir, 12, 1996, pp. 4723-4730.

Leopold et al., "Growth, conductivity, and vapor response properties of metal ion-carboxylate linked nanoparticle films," Faraday Discuss., 125, 2004, pp. 63-76.

Lewis, N. S., "Comparisons between Mammalian and Artificial Olfaction Based on Arrays of Carbon Black-Polymer Composite Vapor Detectors," Acc. Chem. Res., 37, 2004, pp. 663-672.

Lin et al., "A Porous Silicon-Palladium Composite Film for Optical Interferometric Sensing of Hydrogen," Langmuir, 20, 2004, pp. 5104-5108.

Luo et al., "Thermal Activation of Molecularly-Wired Gold Nanoparticles on a Substrate as Catalyst," J. Am. Chem. Soc., 124, 2002, pp. 13988-13989.

Luo et al., "Spectroscopic Characterizations of Molecularly linked Gold Nanoparticle Assemblies upon Thermal Treatment," Langmuir, 20, 2004, pp. 4254-4260.

Luongo et al., "Development of a highly sensitive porous Si-based hydrogen sensor using Pd nano-structures," Sens. Actuators B, 111-112, 2005, pp. 125-129.

Lutz et al., "Hydrogen Sensing by Enzyme-Catalyzed Electrochemical Detection," Anal. Chem., 77, 2005, pp. 4969-4975.

Marubayashi et al., "Monolayer-Protected Au Cluster (MPC)-Supported Ti-BINOILate complex," Org. Lett, 5, 2003, pp. 4409-4412.

Mitsubayashi et al., "Gas-Phase Biosensor for Ethanol," Anal. Chem, 66, 1994, pp. 3297-3302.

Mizsei et al., "Structural transformations of ultra-thin sputtered Pd activator layers on glass and $SnO_2$ surfaces," Thin Solid Films, 391, 2001, pp. 209-215.

Morris et al., "Effects of hydrogen absorption on the electrical conduction of discontinuous palladium thin films," Int. J. Electronics, 81, 1996, pp. 441-447.

Niu et al., "Size-Selective Hydrogenation of Olefins by Dendrimer-Encapsulated Palladium Nanoparticles," J. Am. Chem. Soc., 123, 2001, pp. 6840-6846.

Norrod et al., "Ozone-Induced Oxidation of Self-Assembled Decanethiol: Contributing Mechanism for "Photooxidation"?," J. Am. Chem. Soc., 120, 1998, pp. 2656-2657.

Pang et al., "Humidity effect on the monolayer-protected gold nanoparticles coated chemiresistor sensor for VOCs analysis," Talanta, 65, 2005, pp. 1343-1348.

Pavlou et al., "Sniffing out the Truth: Clinical Diagnosis Using the Electronic Nose," Clin. Chem. Lab. Med., 38, 2000, pp. 99-112.

Poirier et al., "Molecular-Scale Characterization of the Reaction of Ozone with Decanethiol Monolayers on Au(111)," J. Am. Chem. Soc., 121, 1999, pp. 9703-9711.

Pundt A. et al., "Hydrogen and Pd-clusters," Mater. Sci. Eng., B108, 1004, pp. 19-23.

Qi et al., "Toward Large Arrays of multiplex Functionalized Carbon Nanotube Sensors for Highly Sensitive and Selective Molecular Detection," Nano Lett. 3, 2003, pp. 347-351.

Raber et al., "Technology Challenges in Responding to Biological or Chemical Attacks in the Civilian Sector," Science, 302, 1003, pp. 1350-1354.

Rakow et al., "A colorimetric-sensor array for odour visualization," Nature, 406, 2000, pp. 710-713.

Ramachandran et al., "An Overview of Industrial Uses of Hydrogen," Int. J. Hydrogen Energy, 23, 1998, pp. 593-598.

Rao et al., "Synthesis and characterization of lower size, laurylamine protected palladium nanoparticles," Materials Letters, 60, 1006, p. 3169.

Sachtler et al., "On the mechanism of catalytic hydrogenation of nitriles to amines over supported metal catalysts," Applied Catalysis A, 182, 1999, pp. 365-378.

Sakamoto et al., "Electrical resistance measurements as a function of composition of palladium-hydrogen (deuterium) systems by a gas phase method," Phys. : Condens. Matter, 8, 1996, pp. 3399-3411.

Santhanam et al., "Microcontact Printing of Uniform Nanoparticle Arrays," Nano Lett., 4, 2004, pp. 41-44.

Sayago et al., "Hydrogen sensors based on carbon nanotubes thin films," Synthetic Metals, 148, 2005, pp. 15-19.

Schalpbach et al., "Hydrogen-storage materials for mobile applications," Nature, 414, 2001, pp. 353-358.

Schoenfisch et al., "Air Stability of Alkanethiol Self-Assembled Monolayers on Silver and Gold Surfaces," J. Am. Chem. Soc. 120, 1998, pp. 4502-4513.

Senesac et al., "Analyte species and concentration identification using differentially functionalized microcantilever arrays and artificial neural networks," Analyt. Chim. Acta, 558, 2006, pp. 94-101.

Sheng et al., "Voltage-Induced Tunneling Conduction in Granular Metals at Low Temperatures," Phys. Rev. Lett., 28, 1972, pp. 34-37.

Shimizu et al., "Size Evolution of Alkanethiol-Protected Gold Nanoparticles by Heat Treatment in the Solid State," Phys. Chem. B, 107, 2003, pp. 2719-2724.

Sih et al., "Surface-plasmon resonance sensing of alcohol with electrodeposited polythiophene and gold nanoparticle-oligothiophene films," J. Appl. Phys., 98, 2005, pp. 114314-114314-4.

Smith et al., "Principles of quartz crystal microbalance/heat conduction calorimetry: Measurement of the sorption enthalpy of hydrogen in palladium," Thermochim. Acta, 432, 2005, pp. 202-211.

Snow et al., "Self-assembly of gold nanoclusters on micro- and nanoelectronic substrates," Mater. Chem., 12, 2002, pp. 1222-1230.

Su et al., "A Study of the dynamics of Pd Oxidation and PdO Reduction by $H_2$ and $CH_4$," Catal., 176, 1998, pp. 125-135.

Sun et al., "Ag Nanowires Coated wtih Ag/Pd Alloy Sheaths and Their Use as Substrates for Reversible Absorption and Desorption of Hydrogen," J. Am. Chem. Soc., 126, 2004, pp. 5940-5941.

Templeton et al., "Monolayer-Protected Cluster Molecules," Acc. Chem. Res., 33, 2000, pp. 27-36.

Terrill et al., "Monolayers in Three Dimensions: NMR, SAXS, Thermal, and Electron Hopping Studies of Alkanethiol Stabilized Gold Clusters," J. Am. Chem. Soc., 117, 1995, pp. 12537-12548.

Varghese et al., "Extreme Changes in the Electrical Resistance of Titania nanotubes with Hydrogen Exposure," Adv. Mater., 15, 2003, pp. 624-627.

Varghese et al., "Hydrogen sensing using titania nanotubes," Sens. Actuators B, 93, 2003, pp. 338-344.

Vossmeyer et al., "Gold Nanoparticle/Polyphenylene Dendrimer Composite films: Preparation and Vapor-Sensing Properties," Adv. Mater., 14, 2002, pp. 238-242.

Walter et al., "Palladium Mesowire Arrays for Fast Hydrogen Sensors and Hydrogen-Actuated Switches," Anal. Chem., 74, 2002, pp. 1546-1553.

Wang et al., "Array of Molecularly Mediated Thin Film Assemblies of Nanoparticles: Correlation of Vapor Sensing with Interparticle Spatial Properties," J. Am. Chem. Soc., 129, 2007, pp. 2161-2170.

Wohltjen et al., "Colloidal Metal-Insulator-Metal Ensemble Chemiresistor Sensor," Anal. Chem., 70, 1998, pp. 2856-2859.

\* cited by examiner

CHEMICAL SENSORS FOR DETECTING VOLATILE ORGANIC COMPOUNDS AND METHODS OF USE

RELATED APPLICATIONS

The presently-disclosed subject matter claims the benefit of U.S. Provisional Patent Application Ser. No. 60/952,125, filed Jul. 26, 2007; the disclosure of which is incorporated herein by reference in its entirety.

GOVERNMENT INTEREST

Subject matter described herein was made with U.S. Government support under Grant Number CHE0518561 awarded by the National Science Foundation. The government has certain rights in the described subject matter.

TECHNICAL FIELD

The presently-disclosed subject matter relates to sensors and methods for detecting volatile organic compounds. In particular, the presently-disclosed subject matter relates to sensors and methods for detecting volatile organic compounds wherein the conductivity of a chemiresistant film is increased upon exposure to volatile organic compounds.

BACKGROUND AND GENERAL CONSIDERATIONS

Sensing of volatile organic compounds (VOCs) is widely required in a number of applications that range from medicine to environmental pollution. For example, in medical diagnosis, air exhaled by patients may be used to indicate lung cancer by the levels of various VOCs. Further, the presence of uncontrolled diabetes can be indicated by a sweet odor that is due to excess acetone vapor in the breath [1]. With regard to environmental issues, such as the global increase in ozone ($O_3$) and other photochemical oxidants, many of these issues are related to VOCs-Nitric Oxide ($NO_x$) levels, as well as levels of other air pollutants. Ozone is a source of hydroxyl (OH) radicals which react rapidly with most air pollutants ($NO_x$, $SO_x$, CO, etc.), leading to the formation of VOCs that are linked to air contaminants [2]. Further, some polycyclic aromatic hydrocarbons (PAHs) are carcinogenic VOCs generated by incomplete combustion of mobile sources, electricity generating power plants, and coal combustion. Also, emissions indirectly linked to VOCs correspond to particulate matter (PM), which coexists in a mixture with sulfates, nitrates and organics to form VOCs [2].

Terrorism is associated with the use of explosives and chemical or biological warfare agents. In the area of homeland security, detection of explosive vapors, including vapors of volatile organic compounds, is desirable in airports, underground transportation, and other susceptible areas. In particular, significant attention is being paid to chemical warfare agents such as organophosphates [3]. As such, responding to a chemical or biological attack requires the ability to rapidly detect the agents, including VOCs that may be present.

In concerns of public safety, detection and quantification of ethanol vapors in breath (breathalyzers) is required for drivers under the influence of alcohol [4,5]. Breath and blood alcohol concentrations are linearly correlated in a partition ratio of 2000 and breath and blood alcohol content are relative to the degree of alcohol intoxication. For instance, levels of intoxication are legally considered to be between 0.5-1.0 $g \cdot L^{-1}$ in blood, which corresponds to 0.25 to 0.5 $mg \cdot L^{-1}$ in breath (130-266 ppm v/v) [5]. Sensing ethanol is also widely required in fermentation and distillation, either for process control or for avoiding prolonged alcohol exposure.

Other aspects of detecting VOCs are related to new forms of energy production and involve the detection of methanol in direct methanol fuel cells (DMFC) [6]. Lately, vapor-fed fuel cells are gaining more attention due to some advantages over liquid-fed DMFC. Accordingly, detection of methanol vapor is important for controlling the vapor mixture (methanol+ water) flow concentration in order to achieve optimal fuel cell operation.

Electronic noses (e-noses) are electronic devices capable of detecting gas and vapor analytes [4, 7-11]. The e-noses typically use a sensor array to discriminate different analytes in a way that mimics the olfactory system in humans and animals. However, the sensitivity and discrimination among different analytes, especially in complex samples, still requires improvements to compete with techniques like gas chromatography/mass spectrometry (GC/MS). Different transducers used in e-noses include piezoelectric [12-18], surface plasmon resonance (SPR) [19], fluorescence-based [16,20,123], and chemiresistive sensors. In the family of chemiresistors, metal-oxides [7,22,23], carbon-black polymers [8], carbon nanotubes (CNTs) [24], nanorods [23, 25-44], and gold (Au) nanoparticles [24-38, 45-48] have been reported.

Films of Au monolayer-protected clusters (MPCs) have been used for VOC detection due to their ease of fabrication, low power consumption, and the ability to tailor the surface properties to alter the response to different vapors, which can then discriminate between analytes in an array format [49]. For example, a dual-chemiresistor GC based on Au MPC films for detection of low vapor concentrations ranging from 0.1 to 24 ppm has been used [37], and functionalized Au nanoparticles with OH-terminal ligands have been used to improve the affinity and sensitivity towards polar vapors [43]. These devices have detected ethanol at 10-20 ppm, while others using Au nanoparticles with other ligands reported a lowest detection limit (LOD) for methanol of 620 ppm [38]. Another report on vapor sensing with MPCs showed a LOD for toluene of 2.7 ppm that was obtained through current conversion, filtering, and rectification [41].

Accordingly, there remains a need in the art for improved sensors and methods for detecting VOCs. In particular, there is a need for more sensitive and selective sensors and methods for detecting VOCs that are capable of high sensitivity, fast response, reproducibility, and stability.

SUMMARY

This Summary lists several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments of the presently-disclosed subject matter, a sensor for detecting a volatile organic compound (VOC) is provided. In some embodiments, the sensor comprises an electrically insulating support; at least two electrodes positioned at a distance from one another and affixed to the support; and, a chemiresistant film deposited at least between the electrodes and comprising surfactant-coated metal alloy nanoparticles, wherein the surfactant is a compound of Formula (I): $[CH_3(CR_1R_2)_n]_4NR_3$; where n is an integer from 3 to 15; $R_1$ and $R_2$ are each independently selected from the group consisting of H, alkyl, or substituted alkyl; and $R_3$ is selected from the group consisting of $Cl^-$, $I^-$, $NO_3^-$, $SO_4^{2-}$, $ClO_4^{2-}$, and $PF_6^-$; and wherein conductivity of the chemiresistant film is increased upon exposure to the volatile organic compound. In some embodiments, the surfactant is tetraoctylammonium bromide (TOABr).

In some embodiments of the sensors of presently-disclosed subject matter, the chemiresistant film further comprises alkyl-coated metal alloy nanoparticles. In some embodiments, the alkyl comprises about 6 to about 12 carbons atoms. In some embodiments, the alkyl comprises about six carbon atoms.

In some embodiments of the presently-disclosed subject matter, a sensor for detecting a volatile organic compound is provided, wherein the chemiresistant film comprises alkylthiolate-coated metal alloy nanoparticles and surfactant molecules of Formula (I). In some embodiments, the surfactant molecules are tetraoctylammonium bromide (TOABr) molecules. In some embodiments, the alkylthiolate is a compound of Formula II: $CH_3—(CR_1R_2)_n—S—$; where n is an integer from 3 to 15, and $R_1$ and $R_2$ are each independently selected from the group consisting of H, alkyl, and substituted alkyl. In some embodiments, the alkylthiolate is $C_6H_{13}S—$.

The presently-disclosed subject matter further provides, in some embodiments, sensors for detecting volatile organic compounds wherein the metal alloy is selected from the group consisting of gold, silver and combinations thereof. In some embodiments, the metal alloy is selected from the group consisting of gold and gold/silver.

In some embodiments of the sensors of the presently-disclosed subject matter, the chemiresistant film is drop-cast deposited at least between the at least two electrodes. In some embodiments, the chemiresistant film is micro-contact printed at least between the at least two electrodes.

In some embodiments of the presently disclosed subject matter, sensors are provided comprised of a support and electrodes that are inert to a volatile organic compound. In some embodiments, the distance between the electrodes is about 100 nanometers to about 1 millimeter. In some embodiments, the distance between the electrodes is about 23 micrometers.

The presently-disclosed subject matter still further provides, in some embodiments, a method for detecting a VOC in a sample. In some embodiments, the method comprises providing a sensor in accordance with the presently-disclosed subject matter; applying a voltage potential between the at least two electrodes; exposing the sensor to a vapor sample; and, monitoring a change in current between the two electrodes to thereby detect a VOC in the sample. In some embodiments, a method is provided that comprises providing a sensor wherein the chemiresistant film comprises alkylthiolate-coated metal alloy nanoparticles and surfactant molecules, and identifying at least two volatile organic compounds present in a vapor sample. In some embodiments, the surfactant molecules are TOABr molecules. In some embodiments of the methods of the presently-disclosed subject matter, the concentration of the VOC in the sample is about 20 parts per million to about 150 parts per million.

In some embodiments of the sensors and methods of the presently-disclosed subject matter, the volatile organic compound is a compound selected from the group consisting of ethanol, methanol, propanol, acetone, and toluene.

Accordingly, it is an object of the presently-disclosed subject matter to provide sensors and methods for detecting volatile organic compounds. This object is achieved in whole or in part by the presently-disclosed subject matter.

An object of the presently-disclosed subject matter having been stated hereinabove, and which is achieved in whole or in part by the presently-disclosed subject matter, other objects and advantages will become evident to those of ordinary skill in the art after a study of the following description of the presently-disclosed subject matter, Figures, and non-limiting Examples.

DETAILED DESCRIPTION

The details of one or more embodiments of the presently-disclosed subject matter are set forth in the accompanying description below. Other features, objects, and advantages of the presently-disclosed subject matter will be apparent from the specification, Figures, and Claims. All publications, patent applications, patents, and other references noted herein are incorporated by reference in their entirety. In case of conflict, the present specification, including definitions, will control.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods and materials are now described.

Following long-standing patent law convention, the terms "a", "an", and "the" refer to "one or more" when used in this application, including the claims. Thus, for example, reference to "a sensor" includes a plurality of such sensors, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods.

The presently-disclosed subject matter includes sensors and methods for detecting a volatile organic compound. The term "volatile organic compound" or "VOC" is used herein to refer to organic compounds whose vapor pressure is sufficiently high such that at room temperature and normal atmospheric pressure the compounds vaporize and enter the surrounding air. VOCs can include, but are not limited to, compounds typically found in organic solvents, certain paint additives, aerosol spray can propellants, fuels (such as gasoline, and kerosene), petroleum distillates, dry cleaning products, as well as various other industrial and consumer products ranging from office supplies to building materials. VOCs are also naturally emitted by a number of plants and trees. Other example of VOCs include, but are not limited to, compounds such as ethanol, methanol, propanol, acetone, toluene, benzene, substituted benzenes, ethylenediamine, formaldehyde, dichloromethane, dichloropropane, chloroform, tetrahydrofuran, diethyl ether, vinyl acetate, tetracholorethanol, methylchlorosilane, methyl mercury, and nitropropane.

In some embodiments of the presently-disclosed subject matter a sensor for detecting VOCs is provided. In some embodiments, the sensor comprises an electrically insulating support, at least two electrodes positioned at a distance from one another and affixed to the support; and, a chemiresistant film deposited at least between the electrodes and comprising surfactant-coated metal alloy nanoparticles; wherein conductivity of the chemiresistant film is increased upon exposure to the volatile organic compound.

The terms "detect," "detecting," and grammatical variations thereof, are used herein to refer to determining the presence or absence and/or measuring the amount of a VOC. As such, "detecting" a VOC can refer to a determination of whether a particular VOC is present or absent in a sample of interest as well as quantifying the amount of a VOC that is present in a sample of interest. For example, to measure the amount of a VOC in a sample, a calibration curve for the VOC of interest can be obtained by measuring the response of an exemplary sensor to known VOC concentrations, e.g. standards. As another example, in complex mixtures containing a VOC of interest, a sensor that is selective to a VOC of interest and that is not affected by interferents in the sample is used and a calibration curve can constructed to quantify the VOC of interest in the sample. Alternatively, the VOC of interest can first be separated from the sample, and then quantified using a calibration curve. Further, to quantify one or more VOCs in a sample, multi-component calibration curves can be used to analyze samples containing known VOC components. As yet another example, if it is unknown which VOCs are present in a sample, sensor arrays and multidimensional mathematical analyses, such as principle component analyses, can be used to quantify one or more VOCs of interest in a sample.

As used herein, the phrase "electrically insulating support" refers to a substrate that resists the flow of electrical current and can be used to support or separate electrical conductors while providing low background conductivity or without allowing current to travel via the support itself. For example, an "electrically insulating support" can include, but is not limited to, substrates comprised of glass, porcelain, composite materials, polymers such as plastics, silicates such as mica, ceramics, and silicon oxide. In some embodiments, the support and the electrodes are inert to VOCs.

The electrodes of the presently-disclosed sensors can be comprised of any electrically conductive material through which an electric current may enter and leave. Such electrodes are known to those of ordinary skill in the art and include, but are not limited to, silver and gold electrodes that can be affixed to a support. The term "affixed" is used herein to refer to the attachment of electrodes to a support. For example, silver electrodes may be affixed to glass by painting the silver electrodes onto a glass support with a clean pipette or sharp metal tip, such as a glass chromatography syringe. As another example, gold electrodes may be fabricated by photolithography and affixed to a silicon support by sputtering and depositing gold over a suitable adhesion layer such as a chromium adhesion layer.

An exemplary sensor of the presently disclosed subject matter typically comprises at least two electrodes. The phrase "at least two electrodes" is used herein to refer to two or more electrodes that are positioned at a distance from one another such that the current running between the two electrodes can be measured. In some embodiments, the distance between the electrodes is about 100 nanometers to about 1 millimeter. In some embodiments, the distance between the electrodes is about 23 micrometers.

A criterion regarding the distance between the at least two electrodes is that the films conduct electricity across the gap between the at least two electrodes. As such, the upper limit of the distance between the at least two electrodes can be set by the appearance of possible discontinuities or breaks in the film that would prevent conductivity. For example, distances of approximately 100 nm can be used for micro-contact printed chemiresistant films as the micro-contact printed chemiresistant films are generally continuous and conductive over this distance, but can have discontinuities over longer distances that prevent conductivity. As another example, drop-cast chemiresistant films are generally continuous over distances from about 100 nm to about 1 mm or more, so conductivity is possible over longer distances.

The phrase "chemiresistant film," as used herein, refers to films of materials whose conductivity changes in the presence of a vapor or gas analyte. Typically, when a vapor or gas analyte partitions into such a film, the vapors or gas analytes diffuse and absorb onto the materials which comprise the film and the resulting change in conductivity is proportional to the amount of vapor absorbed into the film. As such, in some embodiments of the sensors of the presently-disclosed subject matter, the chemiresistant film deposited between the electrodes is comprised of surfactant-coated metal alloy nanoparticles, wherein the surfactant is a compound of Formula (I):

$$[CH_3(CR_1R_2)_n]_4NR_3 \quad (I)$$

wherein n is an integer from 3 to 15; $R_1$ and $R_2$ are each independently selected from the group consisting of H, alkyl, or substituted alkyl; and $R_3$ is selected from the group consisting of $Cl^-$, $I^-$, $NO_3^-$, $SO_4^{2-}$, $ClO_4^{2-}$, and $PF_6^-$; and wherein conductivity of the chemiresistant film is increased upon exposure to the volatile organic compound. In some embodiments, the surfactant is tetraoctylammonium bromide (TOABr).

Without wishing to be bound by theory, it is believed that as vapor analytes contact the chemiresistant films, a variety of mechanisms can lead to enhanced conductivity of the chemiresistant films. The enhanced conductivity can be related to vapor analytes increasingly solvating the films as the analytes come into contact with the films, thus leading to enhanced ionic conductivity, or the enhanced conductivity can be due to an increase in the dielectric properties of the environment, a decrease in the distance between nanoparticles, or a change in the Faradaic current present in the film.

In some embodiments of the presently-disclosed subject matter, a sensor for detecting a volatile organic compound is provided wherein the chemiresistant film comprises surfactant-coated metal alloy nanoparticles as disclosed herein and further comprises alkyl-coated metal alloy nanoparticles. In some embodiments, the alkyl comprises about 6 to about 12 carbon atoms. In some embodiments, the alkyl comprises about 6 carbon atoms. In some embodiments, the alkyl can be a substituted alkyl.

As used herein the term "alkyl" refers to $C_{4-16}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 4 to about 8 carbon atoms (i.e., a $C_{4-8}$ alkyl), e.g., 4, 5, 6, 7, or 8 carbon atoms. "Higher alkyl" refers to an alkyl group having about 10 to about 16 carbon atoms, e.g., 10, 11, 12, 13, 14, 15, or 16 carbon atoms. In certain embodiments, "alkyl" refers, in particular, to $C_{4-16}$ straight-chain alkyls. In other embodiments, "alkyl" refers, in particular, to $C_{4-16}$ branched-chain alkyls.

Alkyl groups can optionally be substituted (a "substituted alkyl") with one or more alkyl group substituents, which can be the same or different. The term "alkyl group substituent" includes, but is not limited to, alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen or alkyl.

Thus, as used herein, the term "substituted alkyl" includes alkyl groups, as defined herein, in which one or more atoms or functional groups of the alkyl group are replaced with another atom or functional group, including, for example, alkyl, substituted alkyl, halogen, aryl, substituted aryl, alkoxyl, hydroxyl, nitro, amino, alkylamino, dialkylamino, sulfate, and mercapto.

Further, as used herein, the terms alkyl and/or "substituted alkyl" include an "allyl" or an "allylic group." The terms "allylic group" or "allyl" refer to the group —$CH_2HC$=$CH_2$ and derivatives thereof formed by substitution. Thus, the terms alkyl and/or substituted alkyl include allyl groups, such as but not limited to, allyl, methylallyl, di-methylallyl, and the like. The term "allylic position" or "allylic site" refers to the saturated carbon atom of an allylic group. Thus, a group, such as a hydroxyl group or other substituent group, attached at an allylic site can be referred to as "allylic."

In some embodiments, a sensor for detecting a volatile organic compound is provided wherein the chemiresistant films are comprised of alklythiolate-coated metal alloy nanoparticles and surfactant molecules of Formula (I). In some embodiments, the surfactant molecules are TOABr molecules. The term "thiol" refers to a sulfur containing —SH group. As such, the term "thiolate" is used herein to refer to a deprotonated thiol group, or —$S^-$. In some embodiments, the alkylthiolate is a compound of Formula II:

$$CH_3—(CR_1R_2)_n—S— \quad (II)$$

where n is an integer from 3 to 15 and $R_1$ and $R_2$ are each independently selected from the group consisting of H, alkyl, and substituted alkyl. In some embodiments, the alkylhiolate is $C_6H_{13}S$—.

In some embodiments, the chemiresistant films of the presently-disclosed subject matter are deposited at least between the two electrodes of the sensors. As used herein, the phrase "at least between" is used to refer to locations where the chemiresistant films are deposited onto the support. For example, the chemiresistant films can be deposited onto the support such that the film is present only in the space between the electrodes. As another example, the chemiresistant films can be deposited on the support such that the film is present in the space between the electrodes and over the electrodes. Further, as another example, the chemiresistant film can be deposited on the support such that the film is present on a substantial portion of the support including, but not limited to, the space between the electrodes, over the electrodes, and over other areas of the support.

In some embodiments of the sensors of the presently-disclosed subject matter, the chemiresistant film is drop-cast deposited at least between the at least two electrodes. In this regard, one or more drops of a solution in which alkylthiolate-coated, alkyl- and/or surfactant-coated metal alloy nanoparticles are solubilized, e.g. with toluene, can be taken and deposited drop wise at least between the two electrodes and allowed to dry until the solvent has evaporated.

In some embodiments of the sensors of the presently-disclosed subject matter, the chemiresistant film is micro-contact printed at least between the two electrodes. In this regard, a solution comprising coated nanoparticles can be used as ink for micro-contact printing onto solid substrates [50]. Methods of micro-contact printing are known to the skilled artisan and include, but are not limited to, inking a patterned polydimethylsiloxane (PDMS) stamp with featured lines (e.g., lines approximately 1.3 µm wide, approximately 0.5 µm long, with approximately 2.2 µm separation) with a chemiresistant film solution, allowing the solution to dry for several minutes, and then bringing the stamp into contact with a support for several seconds.

The term "metal alloy nanoparticles" is used herein to refer to nanoparticles comprised of at least two elements, one of which is a metal. The term "nanoparticles" includes particles having an average size of, in some embodiments, between about 2 and about 100 nm, in some embodiments, between about 2 and about 50 nm and, in some embodiments, between about 2 and about 10 nm. A metal alloy of the presently-disclosed subject matter can be comprised of a pure metal alloy or mixtures of metal alloys. For example, the metal alloy can be a core/shell particle that contains one metal in the core and another metal as a surrounding shell. As another example, the metal alloy can be a mixed alloy that is an even mixture of two metals throughout the particle. As yet another example, the metal alloy can be a phase-segregated alloy, where the metal alloy has different separate phases of each metal in the nanoparticle, but are not necessarily arranged as a core and shell.

In accordance with the presently-disclosed subject matter the metal alloy nanoparticles can comprise a roughly spherical core that is surrounded by an organic monolayer, which, in some embodiments can comprise a surfactant, an alkyl group, or an alkylthiolate group. In this regard, the term "metal alloy nanoparticles" can be used interchangeably with the phrase "monolayer protected clusters" or "MPCs." Further, the metal alloy nanoparticles surrounded by the organic monolayer can be taken from a solution in which they are soluble and then deposited as films between electrodes where conductivity of the film is then increased upon exposure to volatile organic compounds.

In some embodiments of the presently-disclosed subject matter, the metal alloy is selected from the group consisting of gold, silver, palladium and combinations thereof. Further, in some embodiments, the metal alloy is selected from the group consisting of gold and gold/silver.

The presently-disclosed subject matter still further provides, in some embodiments, a method for detecting a VOC in a sample. In some embodiments, the method comprises providing a sensor in accordance with the presently-disclosed subject matter; applying a voltage potential between the at least two electrodes; exposing the sensor to a vapor sample; and monitoring a change in the current between the two electrodes to thereby detect a VOC in the sample. In some embodiments, the concentration of the VOC in the sample is about 20 parts per million to about 150 parts per million.

In some embodiments, a method for detecting a VOC is provided wherein a sensor is provided that is comprised of a chemiresistant film comprised of a mixture of surfactant molecules and alkylthiolate-coated metal alloy nanoparticles to thereby identify at least two VOCs present in a vapor sample. In some embodiments, the surfactant molecules are TOABr molecules. Disclosed herein in the Examples are data showing that mixed chemiresistant films of alkylthiolate-coated metal alloy nanoparticles and TOABr molecules can be used to alter the selectivity of the films such that the sensors are capable of discriminating among vapors of similar characteristics.

EXAMPLES

The following Examples have been included to illustrate modes of the presently-disclosed subject matter. In light of the present disclosure and the general level of skill in the art, those of skill will appreciate that the following Examples are intended to be exemplary only and that numerous changes, modifications, and alterations can be employed without departing from the scope of the presently-disclosed subject matter.

Example 1

Synthesis of TOABr Au Nanoparticles

TOABr-stabilized Au nanoparticles are chemically synthesized following the Brust method but without the addition of thiols [51]. Briefly, 0.06 g of $HAuCl_4$ was dissolved in 25 mL of water and 0.12 g of tetraoctylammonium bromide (TOABr) was dissolved in 100 mL of toluene. The two solutions were combined and stirred until all of the $AuCl_4^-$ transferred into the toluene phase. The solution turned black after 10-fold excess of $NaBH_4$ with respect to Au was added to the toluene solution with stirring. The average diameter of TOABr-coated Au nanoparticles was 4.1±0.8 nm as determined by atomic force microscopy (AFM) measurements.

Example 2

Film Deposition and Treatment

TOABr-stabilized nanoparticles are insoluble when isolated as a powder [52]. Thus, after reduction and separation from the water phase, the toluene solution containing the particles was reduced to approximately 50 mL by rotary evaporation, filtered with a microdisc filter (acrodisc, 2 μm PTFE membrane) to remove insoluble materials, and then used from solution. Two drops of TOABr-coated Au nanoparticles were drop-cast as a film between gold electrodes that were microfabricated in a clean room. The films were allowed to dry and further used for conductivity measurements.

Example 3

Vapor Sensing

Vapor sensing experiments were performed by monitoring film current with time using a CH Instrument 660A electrochemical workstation operating in chronoamperometry mode. Measurements were made at room temperature and atmospheric pressure. The current was monitored with time while a −0.3 V potential was applied between the two electrodes and the sample was exposed to alternating flows of pure $N_2$ and different concentrations of vapor/$N_2$. Concentrations for the volatile organic compound vapors ranged from 15 to 0.04% and were obtained by the use of flow meters located between the sample and gas cylinders. The flow meters were operated manually by a 3-way valve.

Example 4

Post Deposition Film Treatment

To exchange the coated nanoparticles with mercaptoethanol, a drop-cast film of coated Au nanoparticles was placed above 5 mL of pure mercaptoethanol solution for 24 hrs.

Example 5

Characterization of Films

Films of $C_6H_{13}S$-coated Au nanoparticles and TOABr-coated Au nanoparticles were drop-cast deposited onto Si(100)/TiW (50 Å)/Au(2000 Å) and Si/SiOx substrates for surface reflectance Fourier Transform Infrared (FTIR) spectroscopy and AFM experiments, respectively. FTIR data were acquired using a Digilab FTS 7000 spectrometer (Varian, Cambridge, Mass.) in reflectance mode with a liquid $N_2$-cooled MCT detector. A clean Si/SiOx surface was functionalized with aminopropyltriethoxysilane (APTES). TOABr Au nanoparticles were diluted with a toluene solution by a factor of 1,000, drop-cast deposited on the Si/SiOx substrate, and allowed to dry for AFM characterization. AFM images for nanoparticle size measurements were acquired with a Veeco Digital Instruments Nanoscope 3A Multimode Scanning Probe Microscope (Santa Barbara, Calif.) using a Si tip operating in tapping mode.

Discussion of Examples 1-5

Figure 1:
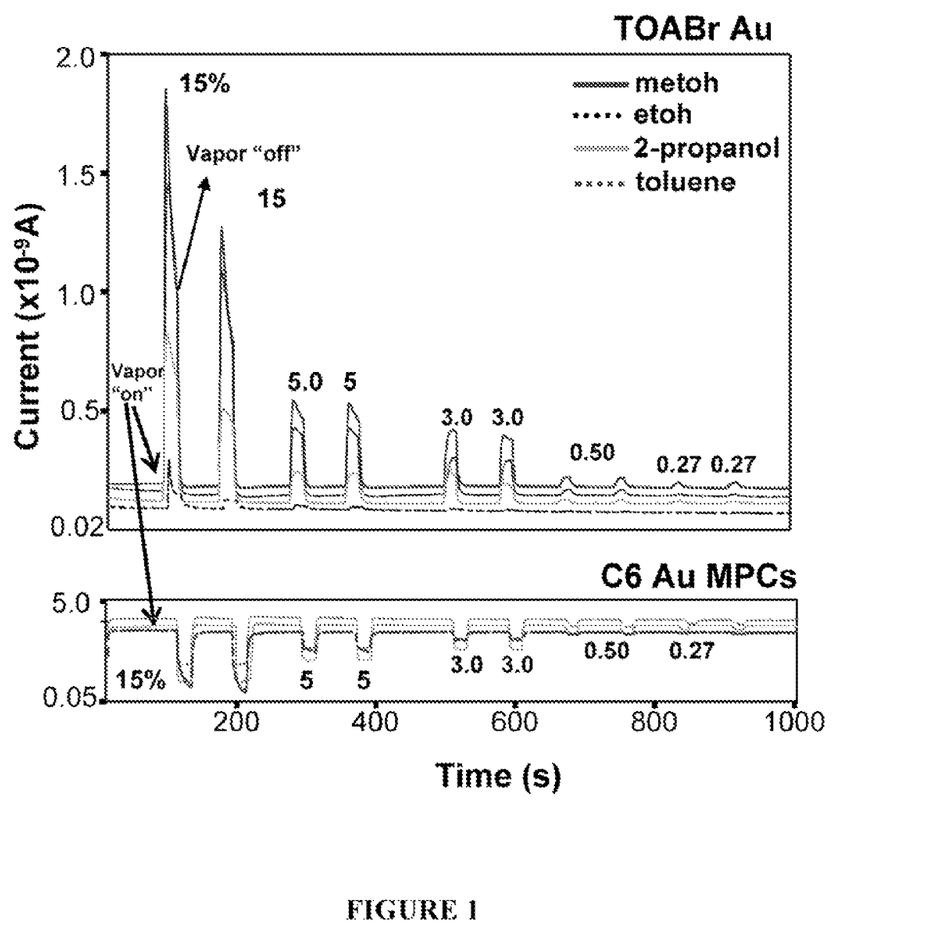
FIG. 1 includes chronoamperometry plots (CA) (current vs. time) for TOABr-coated Au nanoparticles (TOABr Au) exposed to methanol, ethanol, 2-propanol (IPA), and toluene from 15 to 0.27% vapor concentration as indicated, and $C_6H_{13}S$-coated Au nanoparticle film (C6 Au MPC) exposed to the same concentrations of vapors as above but without methanol.
Figure 2:
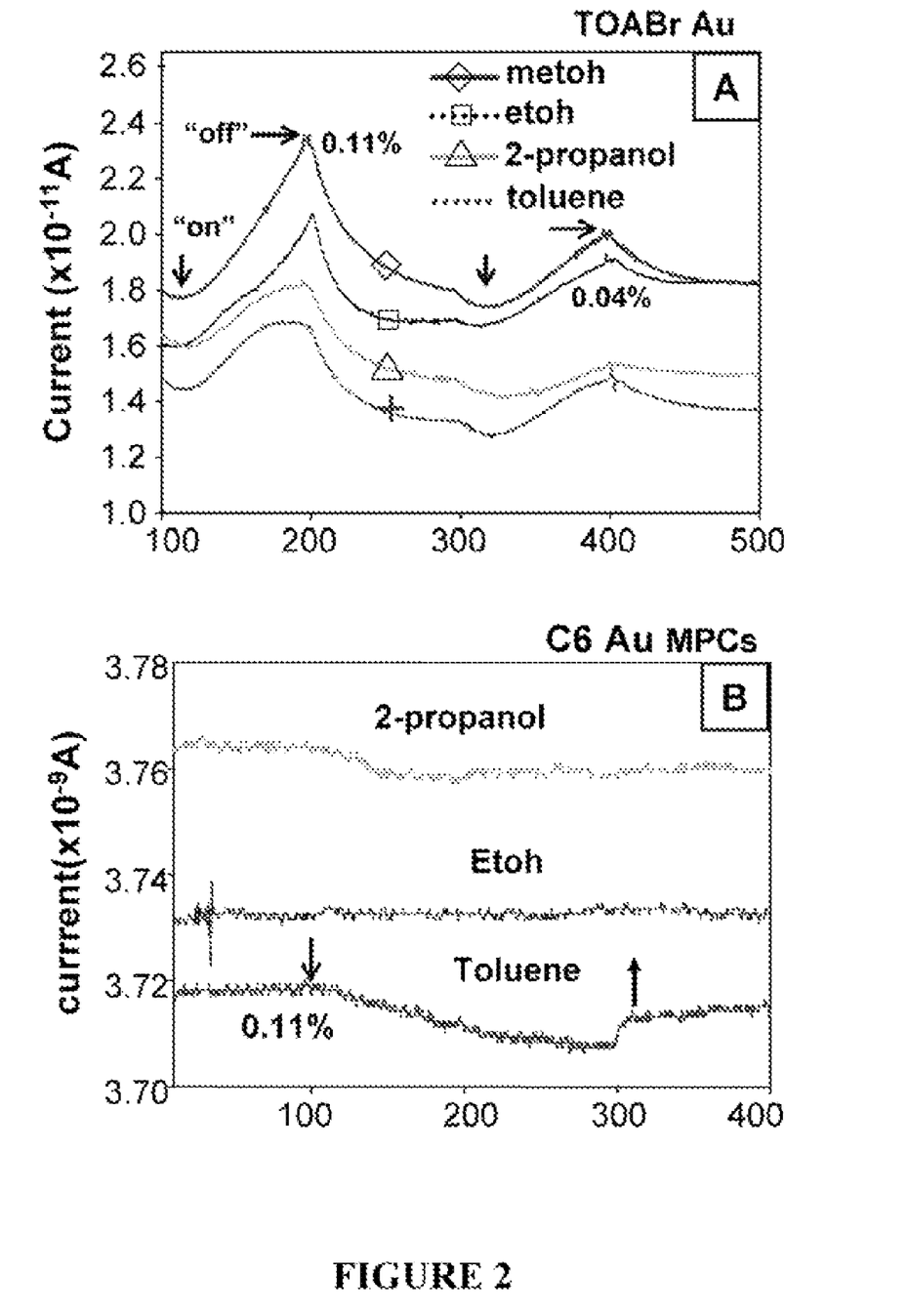
FIGS. 2A and 2B are CA plots (current vs. time) for TOABr-coated Au nanoparticles (TOABr Au) exposed to four different vapors at 0.11% and 0.04% vapor concentration as indicated (FIG. 2A) and $C_6H_{13}S$-coated Au nanoparticle film (C6 Au MPCs) exposed to IPA, methanol, and toluene at 0.11% vapor concentration in a mixture with $N_2$ as indicated (FIG. 2B).

FIG. 1 shows a chronoamperometry (CA) plot (current versus time) for a selected film of TOABr-coated Au nanoparticles and films of $C_6H_{13}S$-coated Au nanoparticles during exposure to methanol, ethanol, 2-propanol (IPA), and toluene from 15% down to 0.27% saturation in $N_2$ carrier gas. This sensor demonstrates great sensitivity to vapor analytes with detection limits of 12, 2, 3, and 37 parts per million (ppm) achieved for ethanol, methanol, IPA, and toluene, respectively. Vapor "off" correlates with exposures to 100% $N_2$ and vapor "on" correlates with exposure to vapor at the percent indicated in the vapor/$N_2$ mixture. FIG. 2 shows an expanded CA plot at the lower vapor concentrations (0.11-0.04%). There are three differences between the two different films. First, films of TOABr-coated Au nanoparticles increase in current in the presence of vapors while films of $C_6H_{13}S$-coated Au nanoparticles decrease in current. Second, the response for films of TOABr-coated Au nanoparticles increases with increasing polarity while, it decreases with increasing polarity of analyte for films of $C_6H_{13}S$-coated Au nanoparticles. Third, the sensitivity is much higher for TOABr-coated Au nanoparticle films.

Increased conductivity for Au MPC films in the presence of polar vapors has been observed [38,41]. Non-polar $C_8H_{17}S$-coated Au nanoparticles drop-cast deposited on interdigitated electrodes [41], alkanethiols functionalized with OH-terminal groups[41], and Au clusters linked by dithiol bridges [38] have shown increased conductivity upon exposure to polar vapors, but the reason was unclear. This was recently attributed to ionic currents present in remaining TOABr impurities after the synthesis was completed [39]. For example, at 3.0%, the response of TOABr-coated Au nanoparticle films is highest for methanol which is 103%. The highest response at the same percent vapor is for toluene for $C_6H_{13}S$-coated Au nanoparticle films, which is much smaller at 12%. In this regard, it should be noted that the percent response at $\geq 3\%$ for the majority of polar vapors for films of TOABr-coated Au nanoparticles, exceeds 100%.

FIG. 2 shows that all vapors examined are detected with TOABr-coated Au nanoparticle films at 0.04% saturation, while only toluene is barely detected at 0.11% with $C_6H_{13}S$-coated Au films. Unpurified (two-phase synthesis) dithiol-linked Au nanoparticle films displayed both increased conductivity upon exposure to water vapors and reduced sensitivity for toluene in the presence of the same vapor [38]. The partitioning of vapors into the film results in both the film swelling and changes in dielectric constant (medium permittivity) [53] and can be described by the following equation:

$$\sigma_{EL}(\delta e, T) = \sigma 0 \exp[-\beta_d \delta_e] \exp[E_A/RT] \quad (1)$$

where "$\sigma_{EL}$" is the conductivity of the coated-nanoparticle film, "$\delta_e$" the core-to-core distance, "$\beta_d$" a quantum mechanical tunneling factor typically on the order of $1 \text{Å}^{-1}$ and "$E_A$" is the activation energy barrier which neutral cores should overcome in order to be positively or negatively charged during electron transport. The $E_A$ is expressed as follows:

$$E_A \approx e^2/4\pi \in_r \in_0 r \quad (2)$$

where "$\in_0$" and "$\in_r$" are the vacuum permittivity and relative permittivity of the dielectric medium surrounding the metal core, respectively, and "r" corresponds to the radius of the metal particle. The decrease in current can be explained by an increase in $\delta_e$ in the first exponential term in Equation 1, which occurs when vapor molecules partition into the film and increase the distance between particles by overall film swelling.

The extent of vapor phase partitioning and film swelling depends on the functionality of the coated nanoparticles and the characteristics of the analyte. Polar analytes will like polar coated-nanoparticles and non-polar analytes will like non-polar coated-nanoparticle and cause larger amounts of swelling. An increase in current in the presence of an analyte can be due to three possibilities according to Equation 1, (1) a decrease in $\delta_e$ or film contraction, (2) a decrease in $E_A$ due to an increase in $\in_r$, or (3) a decrease in $\beta_d$. An increase in $\in_r$ could occur upon partitioning of a polar analyte into a non-polar medium. In the case of TOABr-coated nanoparticle films, an increase in $\in_r$ is expected with increasing polarity of the analyte, which is consistent with a decrease in $E_A$ in the electron hopping equation and increase in conductivity (current). However, cyclic voltammograms (CVs) of TOABr-coated Au nanoparticle films show significant hysteresis indicative of large ionic currents in these films (data not shown). Since the current is largely ionic, the electron hopping equation likely does not apply and the sensing mechanism is different. Without wishing to be bound by theory, it is believed that several mechanisms can lead to the enhanced conductivity of the films. It is possible that more polar analytes solvate the film better, leading to enhanced ionic conductivity as observed for solid-state electrochemistry experiments of plasticized films [54]. Other possibilities include changes in the dielectric constant of the environment, decreases in the distance between nanoparticles, and Faradaic electrochemical reactions in the films. This different sensing mechanism compared to the more common swelling mechanism for alkanethiol-coated films has led to a different response direction that is more sensitive and has a lower detection limit (LOD). Even toluene partially solvated the TOABr-coated Au nanoparticle films due to the non-polar octyl groups.

Figure 3:
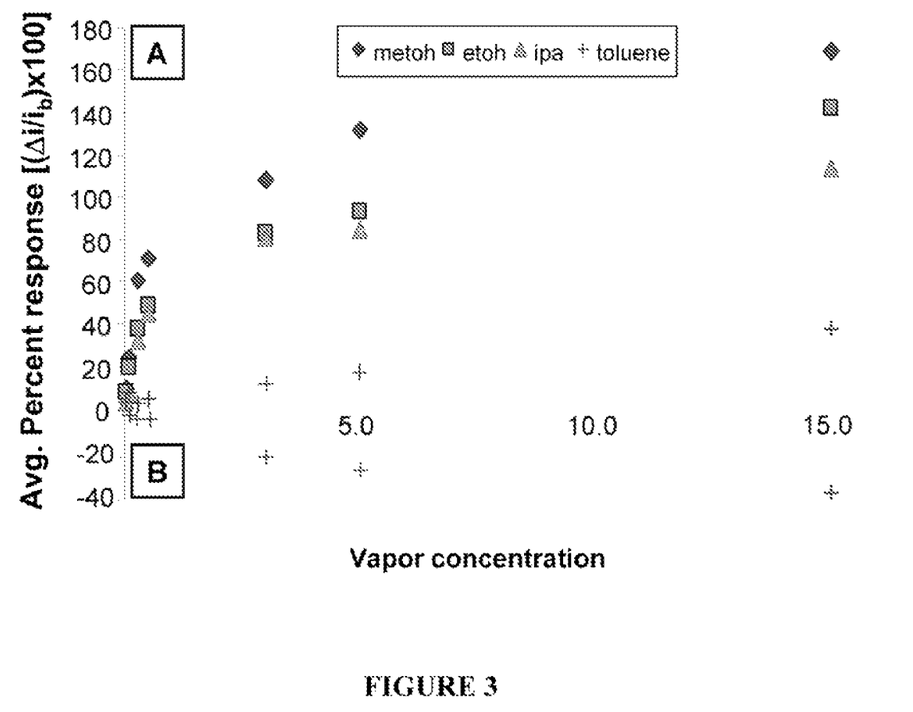
FIG. 3 includes calibration curves showing average percent response versus vapor concentration (0.04 to 15%) for methanol, ethanol, IPA, and toluene for (A) TOABr-coated Au nanoparticles and versus 0.11 to 15% toluene vapor for (B) $C_6H_{13}S$-coated Au nanoparticle film. The dots represent the average of three devices.

FIG. 3 shows the average calibration points plotting the percent response (y-axis) versus the vapor concentration (x-axis) for TOABr-coated Au nanoparticles and $C_6H_{13}S$-coated Au nanoparticle films. The $C_6H_{13}S$-coated Au nanoparticle films were only exposed to toluene for comparison purposes (FIG. 3, B). The points represent the average of three samples and standard deviations are omitted for clarity.

The following trend for relative dielectric constants 33, 24, 18, and 2.4 correlates well with the decreased average percentage responses seen in FIG. 3 for methanol, ethanol, IPA, and toluene, respectively. At high vapor concentrations (approximately 15%), the films (except toluene) responded with values above 100% with a 2-3 second response time. This was only observed for polar vapors. At low concentrations (from 0.11-0.04%) response time was slower ranging from 40-50 seconds but was still very sensitive as shown in FIG. 2A. The magnitude of percent response to toluene for TOABr-coated Au and $C_6H_{13}S$-coated Au nanoparticles are similar but opposite in current direction as discussed earlier.

These films have been tested for analytes in the presence of potential interferents such as humidity and high temperature. Results show that TOABr-coated Au nanoparticle sensors function after being exposed to 70-80° C. and in the presence of 15% relative humidity (RH). To reduce the cost of the sensor, sensors comprised of TOABr-coated Ag nanoparticles and TOABr Pd/Ag (1:1 mol ratio) were also synthesized. Pure Ag films exhibited no response in the presence of vapors. Interestingly, TOABr-coated Au/Ag films showed enhanced selectivity for polar vapors over non-polar vapors, although the sensitivity to all vapors decreased relative to TOABr-coated Au nanoparticles. This indicates that the metal composition can play an important role in sensing vapors.

Figure 4:
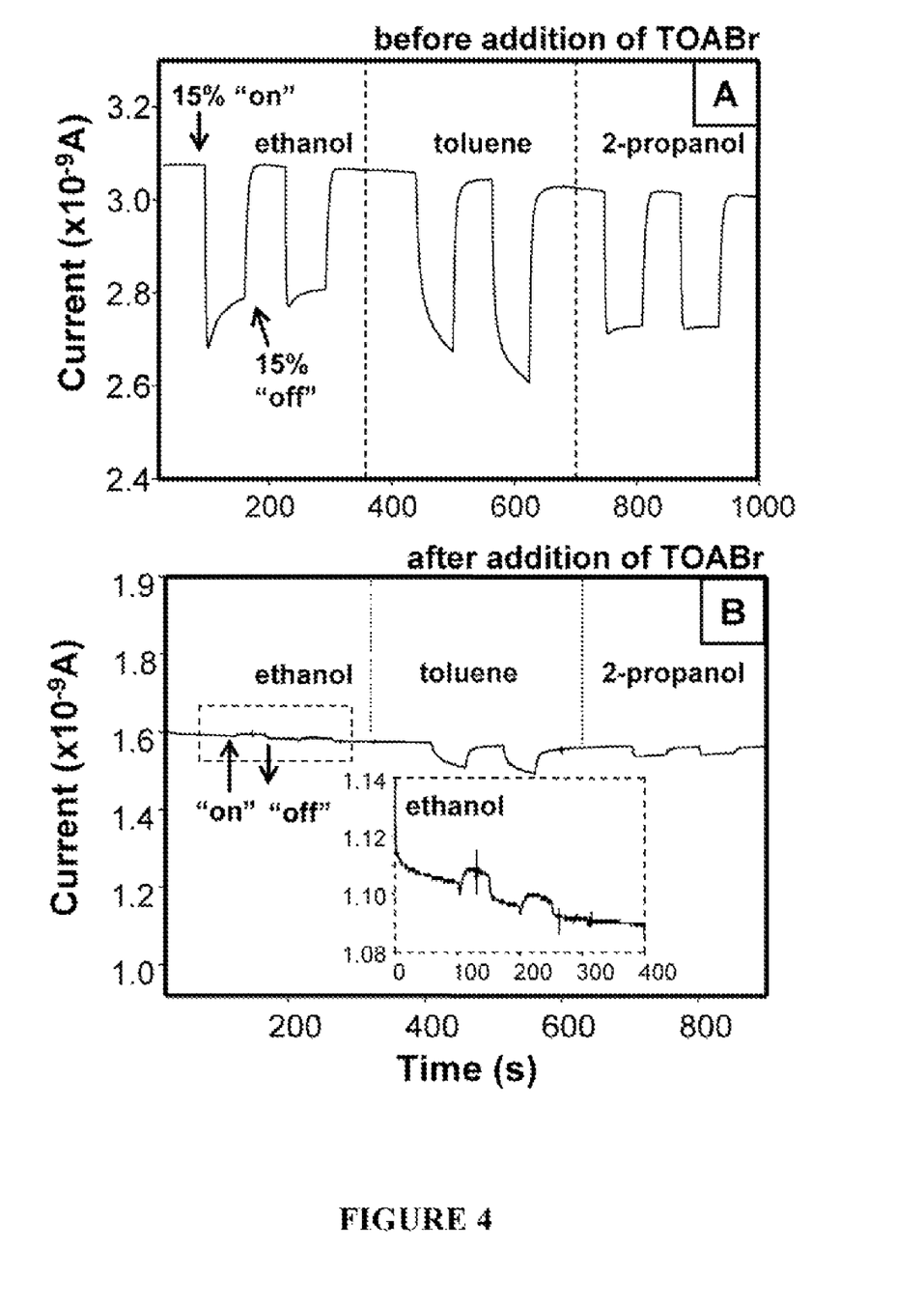
FIGS. 4A and 4B depict chemiresistive responses for $C_6H_{13}S$-coated Au nanoparticle film, before (FIG. 4A) and after (FIG. 4B) addition of TOABr, to ethanol, toluene, and IPA at the indicated concentration.

Films of mixed $C_6H_{13}S$-coated Au nanoparticles with TOABr-coated Au nanoparticles were prepared to determine whether the selectivity of the film to different vapors could be altered. FIG. 4 shows a chemiresistive response to 15% ethanol, toluene, and IPA as indicated for a selected $C_6H_{13}S$-coated Au nanoparticle film before and after addition of TOABr-coated Au nanoparticles to the $C_6H_{13}S$-coated Au nanoparticle solution that was exposed. FIG. 4A shows the typical response observed for $C_6H_{13}S$-coated Au nanoparticles, where the response is largest for toluene, followed by IPA and ethanol.

FIG. 4B shows a chemiresistive plot for the same film where its sensitivity is greatly reduced by the addition of TOABr molecules. TOABr added to $C_6H_{13}S$-coated Au nanoparticles in a 1:5 TOABr:Au molar ratio led to a decrease in overall sensitivity to the VOCs but, favorably altered the selectivity. The response was similar for ethanol and IPA before addition of TOABr, but is now in the opposite direction for the two analytes, making discrimination easier. Despite the fact that sensitivity is affected by the addition of TOABr, this approach demonstrates the design of sensors capable of discrimination among vapors of similar characteristics.

The selectivity of coated Au nanoparticles has been previously altered by changing the functionality of the nanoparticles [48], which has even been used in an array format [49]. However, changing the functionality usually involves synthesizing a new batch of coated nanoparticles with different functional groups or performing solution-phase thiol place-exchange or coupling reactions which can take several days. The studies disclosed herein utilize another approach for altering selectivity by changing the functionality of coated Au nanoparticles using vapor-phase place exchange reactions [55]. Micro-contact printed or microstamped films of $C_6H_{13}S$-coated Au nanoparticle vapor-exchanged with dithiol molecules were previously prepared for imparting stability to the microlines by forming two thiolate-Au bonds on adjacent nanoparticles per dithiol molecule [42]. Further, self-assembled monolayers (SAMs) have been assembled by vapor phase thiol adsorption [56]. The advantage of vapor-phase thiol place-exchange is that one sample of coated Au nanoparticles can be drop-cast across electrodes and chemically altered to various different functionalities very rapidly by eliminating long reactions times, rotaevaporation, filtering, purification, and collection. It also allows functionalization with groups that might cause solution-phase coated nanoparticles to become insoluble which would make drop-casting them as a film impossible.

Figure 5:
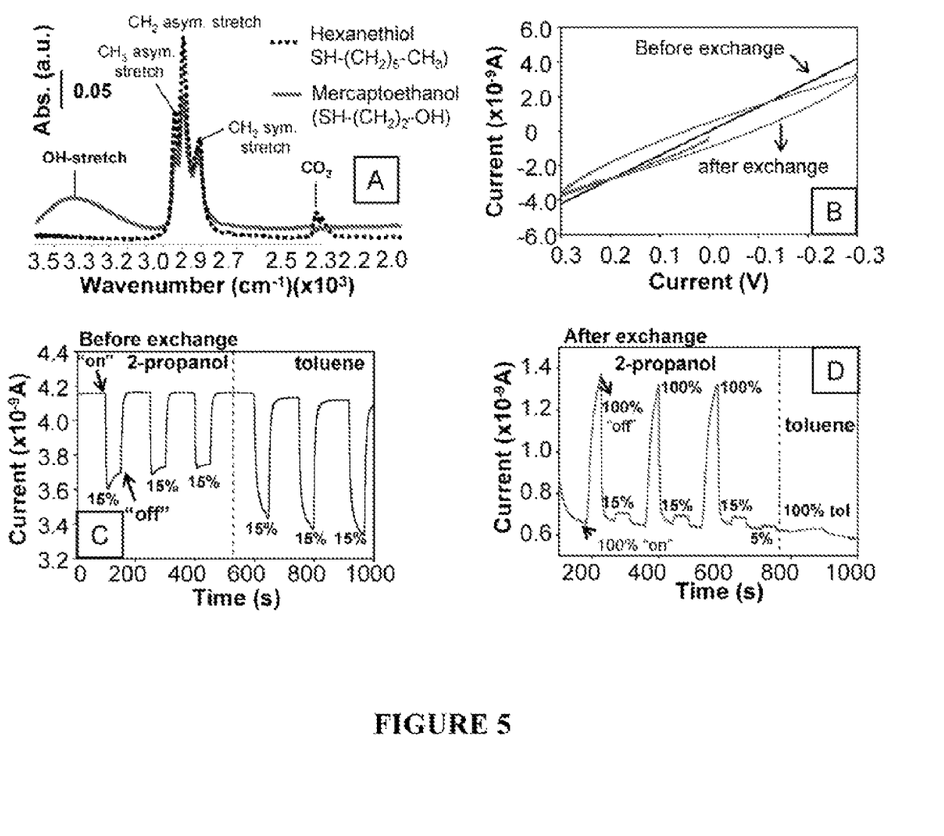
FIG. 5 includes Fourier Transform Infrared (FTIR) spectra for $C_6H_{13}S$-coated Au nanoparticles (black, dotted-line) vapor-phase exchanged for 24 hrs with mercaptoethanol (continuous line) (FIG. 5A); and, cyclic voltammograms (CV) (FIG. 5B) and chronoamperometry (CA) plots (FIGS. 5C and 5D) for selected $C_6H_{13}S$-coated Au nanoparticle films drop-cast deposited on an electrode device before and after exchange, respectively, and exposed to IPA and toluene vapors at the indicated concentrations.
Figure 6:
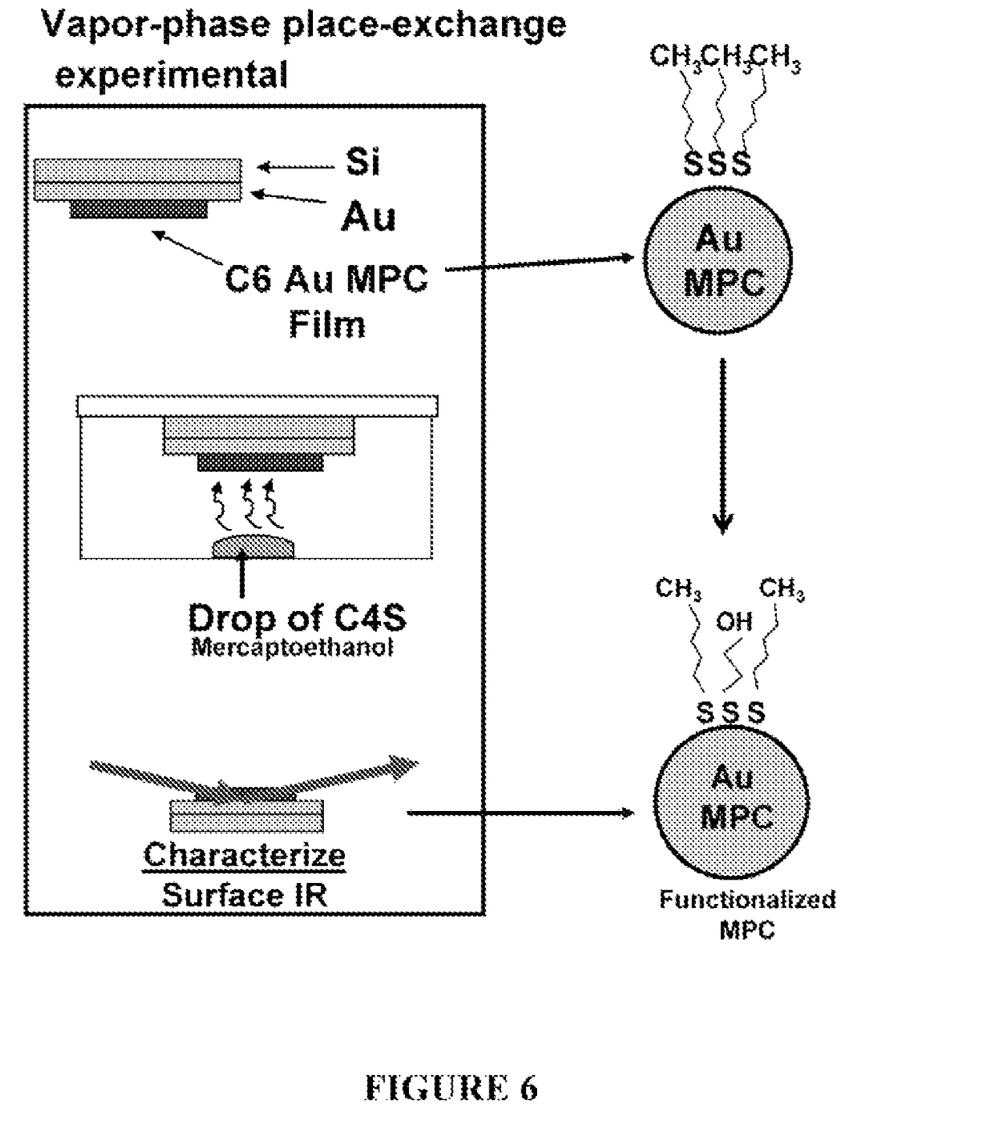
FIG. 6 is a schematic representation of a vapor-phase exchange reaction between a $C_6H_{13}S$-coated Au nanoparticle (C6 Au MPC) and mercaptoethanol ligands.

FIG. 5 shows FTIR, cyclic voltammograms (CVs), and chronoamperometry (CA) plots for a non-polar hexanethiolate ($C_6H_{13}S$—) coated Au nanoparticle film that was vapor-phase exchanged with a more polar and shorter thiol, mercaptoethanol (S—$(CH_2)_2$—OH) for 24 hrs. The FTIR peak developed at approximately 3370 cm$^{-1}$ (FIG. 5A) after place-exchange, which corresponds to an (OH) stretch for the mercaptoethanol molecules, confirming their adsorption to the film. FIG. 5B shows a CV for a selected film of $C_6H_{13}S$-coated Au nanoparticles before and after exchange with mercaptoethanol in the vapor-phase for the time indicated. The current is on the same order of magnitude, but the plot shows considerable hysteresis after exchange, which is consistent with ionic current, as was observed previously for TOABr-coated Pd films [57]. The hysteresis is not as large as the TOABr Au films, though. FIGS. 5C and 5D shows the CA data for the same film before and after exchange, respectively that was exposed to IPA and toluene vapor at the indicated concentrations. The plots before exchange are consistent with alkanethiol-coated Au nanoparticles. As expected, the response is larger for toluene, since the film is non-polar. FIG. 5D shows two further features. First, the current response for both vapors have changed direction (current up) and second, the response for toluene is greatly reduced. This evidence clearly demonstrates the affinity of the film for polar vapors by a vapor-phase exchange method. FIG. 6 shows a schematic representation of $C_6H_{13}S$-coated Au nanoparticles exchanged with more polar mercaptoethanol via vapor-phase place-exchange reaction and the experimental procedure carried out.

The foregoing examples demonstrate the design of a very sensitive film comprised of TOABr-stabilized Au nanoparticles for sensing VOCs. These films are more sensitive to polar VOCs compared to $C_6H_{13}S$-coated Au nanoparticles and can detect, for example, ethanol at levels relevant for breathalyzer tests. Two approaches were used to improve the selectivity for complex mixtures. First, addition of TOABr molecules to $C_6H_{13}S$-coated Au nanoparticles exhibited two different behaviors: the current response increased in the presence of ethanol and decreased for IPA and toluene as expected since the film is also comprised of $C_6H_{13}S$-coated Au nanoparticles. The second approach was to functionalize the $C_6H_{13}S$-coated Au nanoparticle films by exchanging polar groups (mercaptoethanol) in the vapor phase. This led to chemiresistive films that responded selectively to IPA by increasing in current and very poorly responded to the presence of non-polar analytes (toluene). Ionic currents dominate the conductivity of TOABr Au films revealing a new type of sensing mechanism for metal nanoparticles surrounded by organic stabilizers.

REFERENCES

Throughout this application, various publications are referenced. All such references are incorporated herein by reference, including the references set forth in the following list.

[1] Cao, W.; Duan, Y. Clin. Chem. 2006, 52, 800-811.
[2] Finlayson-Pitts, B.; Pitts, J. N. Science 1997, 276.
[3] Raber, E.; Imbro, D. R. Science 2003, 302, 1350-1354.
[4] Strike, D. J.; Meijerink, M. G. H.; Koudelka-Hep, M. Fresenius J. Anal. Chem. 1999, 364, 499-505.
[5] Mitsubayashi, K.; Yokoyama, K.; Takeuchi, T.; Karube, I. Anal. Chem 1994, 66, 3297-3302.
[6] Kim, D. W.; Lee, J. S.; Lee, G. S.; Overzet, L.; Kozlov, M.; Aliev, A. E.; Park, Y. W.; Yang, D. J. Nanosc. Nanotechnol. 2006, 6, 3608-3613.
[7] Albert, K. J.; Lewis, N. S.; Schauer, C. L.; Sotzing, G. A.; Stitzel, S. E.; Vaid, T. P.; Walt, D. R. Chem. Rev. 2000, 100, 2595-2626.
[8] Lewis, F. A. The Palladium/Hydrogen System; Academic Press Inc.: London, 1967.
[9] Gopel, W. Sens. Actuators B. 1998, 52, 125-142.
[10] Pavlou, A. K.; Turner, A. P. F. Clin. Chem. Lab. Med. 2000, 38, 99-112.
[11] Yinon, J. Anal. Chem. 2003, 99A-105A.
[12] Crooks, R. M.; Ricco, A. J. Acc. Chem. Res. 1998, 31, 219-227.
[13] Grate, J. W. Chem. Rev. 2000, 100, 2627-2648.
[14] Datskos, P. G.; Sepaniak, M. J.; Tipple, C. A.; Lavrik, N. Sens. Actuators B 2001, 76, 393-402.
[15] Sepaniak, M.; Datskos, P.; Lavrik, N.; Tipple, C. Anal. Chem. 2002, 568A-575A.
[16] Yang, J.-S.; Swager, T. M. J. Am. Chem. Soc. 1998, 120, 5321-5322.

[17] Silberberg, M. S. *The Molecular Nature of Matter and Change*, 4th ed.: Boston, 2006.
[18] Senesac, L. R.; Dutta, R.; Datskos, P.; Sepaniak, M. *Analyt. Chim. Acta* 2006, 558, 94-101.
[19] Sih, B. C.; Wolf, M. O.; Jarvis, D.; Young, J. F. *J. Appl. Phys.* 2005, 98, 114314.
[20] Drew, S. M.; Janzen, D. E.; Buss, C. E.; MacEwan, D. I.; Dublin, K. M.; Mann, K. R. *J. Am. Chem. Soc.* 2001, 123, 8414-8415.
[21] Bohne, C.; Ihmels, H.; Waidelich, M.; Yinwa, C. *J. A. Chem. Soc.* 2005, 127, 17158-17159.
[22] Dutta, R.; Hines, E. L.; Gardner, J. W.; Kashwan, K. R.; Bhuyan, M. *Sens. Actuators B* 2003, 94, 228-237.
[23] Comini, E.; Yubao, L.; Brando, Y.; Sbervegliery, G. *Chem. Phys. Letters* 2005, 407, 368-371.
[24] Qi, P.; Vermesh, O.; Grecu, M.; Javey, A.; Wang, Q.; Dai, H.; Peng, S.; Cho, K. *J. Nano Lett.* 2003, 3, 347-351.
[25] Zhang, H.-L.; Evans, S. D.; Henderson, J. R.; Miles, R. E.; Shen, T.-H. *Nanotechnol.* 2002, 13, 439-444.
[26] Ahn, H.; Chandekar, A.; Kang, B.; Sung, C.; Whitten, J. E. *Chem. Mater.* 2004, 16, 3274-3278.
[27] Briglin, S. M.; Gao, T.; Lewis, N. S. *Langmuir.* 2004, 20, 299-305.
[28] Zamborini, F. P.; Leopold, M. C.; Hicks, J. F.; Kulesza, P. J.; Malik, M. A.; Murray, R. W. *J. Am. Chem. Soc.* 2002, 124, 8958-8964.
[29] Leopold, M. C.; Donkers, R. L.; Georganopoulou, D.; Fisher, M.; Zamborini, F. P.; Murray, R. W. *Faraday Discuss.* 2004, 125, 63-76
[30] Joseph, Y.; Guse, B.; Yasuda, A.; Vossmeyer, T. *Sens. Actuators B* 2004, 98, 188-195.
[31] Joseph, Y.; Besnard, I.; Rosenberger, M.; Guse, B.; Nothofer, H.-G.; Wessels, J. M.; Wild, U.; Knop-Gericke, A.; Su, D.; Schlogl, R.; Yasuda, A.; Vossmeyer, T. *J. Phys. Chem. B* 2003, 107, 7406-7413.
[32] Joseph, Y.; Krasteva, N.; Besnard, I.; Guse, B.; Rosenberger, M.; Wild, U.; Knop-Gericke, A.; Schlogl, R.; Krustev, R.; Yasuda, A.; Vossmeyer, T. *Faraday Discuss.* 2004, 125, 77-97.
[33] Vossmeyer, T.; Guse, B.; Besnard, I.; Bauer, R. E.; Mullen, K.; Yasuda, A. *Adv. Mater.* 2002, 14, 238-242.
[34] Krasteva, N.; Besnard, I.; Guse, B.; Bauer, R. E.; Mullen, K.; Yasuda, A.; Vossmeyer, T. *Nano Lett.* 2002, 2, 551-555.
[35] Krasteva, N.; Krustev, R.; Yasuda, A.; Vossmeyer, T. *Langmuir* 2003, 19, 7754-7760.
[36] Krasteva, N.; Guse, B.; Besnard, I.; Yasuda, A.; Vossmeyer, T. *Sens. Actuators B* 2003, 92, 137-143.
[37] Cai, Q.-Y.; Zellers, E. T. *Anal. Chem.* 2002, 74, 3533-3539.
[38] Han, L.; Daniel, D. R.; Maye, M. M.; Zhong, C.-J. *Anal. Chem.* 2001, 73, 4441-4449.
[39] Pang, P.; Guo, Z.; Cai, Q. *Talanta* 2005, 65, 1343-1348.
[40] Foos, E. E.; Snow, A. W.; Twigg, M. E.; Ancona, M. G. *Chem. Mater.* 2002, 14, 2401-2408.
[41] Wohltjen, H.; Snow, A. W. *Anal. Chem.* 1998, 70, 2856-2859.
[42] Ibañez, F. J.; Growrishetty, U.; Crain, M. M.; Walsh, K. M.; Zamborini, F. P. *Anal. Chem.* 2006, 78, 753-761.
[43] Evans, S. D.; Johnson, S. R.; Cheng, Y. L.; Shen, T. *J. Mater. Chem.* 2000, 10, 183-188.
[44] Ibañez, F. J.; Gowrishetty, U.; Crain, M. M.; Walsh, K. M.; Zamborini, F. P. *Anal. Chem.* 2006, 78, 753-761.
[45] Lewis, N. S. *Acc. Chem. Res.* 2004, 37, 663-672.
[46] Walter, E. C.; Favier, F.; Penner, R. M. *Anal. Chem.* 2002, 74, 1546-1553.
[47] Wohltjen, H.; Snow, A. W. *Anal. Chem.* 1998, 70, 2856-2859.
[48] Evans, S. D.; Johnson, S. R.; Cheng, Y. L.; Shen, T. *J. Mater. Chem.* 2000, 10, 183-188.
[49] Wang, L.-S.; Xiajing, K.; Karuiki, N. N.; Schadt, M.; Wang, G. R.; Rendeng, Q.; Choi, J.; Luo, J.; Lu, S.; Zhong, C.-J. *J. Am. Chem. Soc.* 2007, 129, 2161-2170.
[50] Xia, Y.; Whitesides, G. M. *Polym. Mater. Sci. Eng.* 1997, 77, 596.
[51] Brust, M.; Walker, M.; Bethell, D.; Schiffrin, D. J.; Whyman, R. *Chem. Comm.* 1994, 7, 801-802.
[52] Isaacs, S. R.; Culter, E. C.; Park, J.-S.; Lee, T. R.; Shon, Y.-S. *Langmuir.* 2005, 21, 5689-5692.
[53] Neugebauer, C. A.; Webb, M. B. *J. Appl. Phys.* 1962, 33, 74.
[54] Choi, J.-P.; Coble, M. M.; Branham, M. R.; DeSimone, J. M.; Murray, R. W. *J. Phys. Chem. C* 2007, 111, 3778-3785.
[55] Hostetler, M. J.; Zhong, C.-J.; Yen, B. K. H.; J, A.; Gross, S. M.; Evans, N. D.; Porter, M.; Murray, R. W. *J. Am. Chem. Soc.* 1998, 120, 9396-9397.
[56] Chailapakul, O.; Sun, L.; Xu, C.; Crooks, R. M. *J. Am. Chem. Soc.* 1993, 115, 12459-12467.
[57] Ibañez, F. J.; Zamborini, F. P. *J. Am. Chem. Soc.,* 2008, 130 (2), 622-633.
[58] Ibañez, F. J.; Zamborini, F. P. *Langmuir* 2006, 22, 9789-9796.

It will be understood that various details of the presently-disclosed subject matter can be changed without departing from the scope of the subject matter disclosed herein. Furthermore, the foregoing description is for the purpose of illustration only, and not for the purpose of limitation.

What is claimed is:

1. A sensor for detecting a volatile organic compound, comprising:
   an electrically insulating support;
   at least two electrodes positioned at a distance from one another and affixed to the support; and
   a chemiresistant film deposited at least between the electrodes and comprising surfactant-coated metal nanoparticles or surfactant-coated metal alloy nanoparticles, wherein the surfactant is a compound of Formula (I):

$$[CH_3(CR_1R_2)_n]_4NR_3 \quad (I)$$

wherein n is an integer from 3 to 15; $R_1$ and $R_2$ are each independently selected from the group consisting of H, alkyl, and substituted alkyl; and $R_3$ is selected from the group consisting of $Cl^-$, $I^-$, $NO_3^-$, $SO_4^{2-}$, $ClO_4^{2-}$, and $PF_6^-$; and wherein conductivity of the chemiresistant film is increased upon exposure to the volatile organic compound.

2. The sensor of claim 1, wherein the surfactant is tetraoctylammonium bromide (TOABr).

3. The sensor of claim 1, wherein the support and the electrodes are inert to the volatile organic compound.

4. The sensor of claim 1, wherein the distance between the electrodes is from about 100 nanometers to about 1 millimeter.

5. The sensor of claim 1, wherein the distance between the electrodes is about 23 micrometers.

6. The sensor of claim 1, wherein the metal alloy comprises a metal selected from the group consisting of gold, silver, and combinations thereof.

7. The sensor of claim 6, wherein the metal alloy is selected from the group consisting of a gold alloy and a gold/silver alloy.

8. The sensor of claim 1, wherein the chemiresistant film is drop-cast deposited at least between the at least two electrodes.

9. The sensor of claim 1, wherein the chemiresistant film is micro-contact printed at least between the at least two electrodes.

10. The sensor of claim 1, wherein the chemiresistant film further comprises alkyl-coated metal nanoparticles or alkyl-coated metal alloy nanoparticles.

11. The sensor of claim 10, wherein the alkyl comprises about 6 to about 12 carbon atoms.

12. The sensor of claim 11, wherein the alkyl comprises about 6 carbon atoms.

13. The sensor of claim 10, wherein the metal alloy comprises a metal selected from the group consisting of gold, silver, and combinations thereof.

14. The sensor of claim 13, wherein the metal alloy is selected from the group consisting of a gold alloy and a gold/silver alloy.

15. The sensor of claim 1, wherein the volatile organic compound is a compound selected from the group consisting of ethanol, methanol, propanol, acetone, and toluene.

16. A method of detecting a volatile organic compound in a sample, comprising:
providing a sensor including:
an electrically insulating support;
at least two electrodes positioned at a distance from one another and affixed to the support; and
a chemiresistant film deposited at least between the electrodes and comprising surfactant-coated metal nanoparticles or surfactant-coated metal alloy nanoparticles, wherein the surfactant is a compound of Formula (I):

$$[CH_3(CR_1R_2)_n]_4NR_3 \qquad (I)$$

wherein n is an integer from 3 to 15; $R_1$ and $R_2$ are each independently selected from the group consisting of H, alkyl, and substituted alkyl; and $R_3$ is selected from the group consisting of $Cl^-$, $I^-$, $NO_3^-$, $SO_4^{2-}$, $ClO_4^{2-}$, and $PF_6^-$; and wherein conductivity of the chemiresistant film is increased upon exposure to the volatile organic compound;

applying a voltage potential between the at least two electrodes;

exposing the sensor to a vapor sample; and monitoring a change in the current between the two electrodes to thereby detect the volatile organic compound in the sample.

17. The method of claim 16, wherein the volatile organic compound is a compound selected from the group consisting of ethanol, methanol, propanol, acetone, and toluene.

18. The method of claim 16, wherein the concentration of the volatile organic compound in the sample is about 20 parts per million to about 150 parts per million.

* * * * *